US00PP08158P

United States Patent [19]

Dehan

[11] Patent Number: Plant 8,158

[45] Date of Patent: Feb. 23, 1993

[54] ASTER PLANT NAMED SUNSHIR

[75] Inventor: Klara Dehan, Holon, Israel

[73] Assignee: Danziger - "Dan" Flower Farm, Post Beit Dagan, Israel

[21] Appl. No.: 687,161

[22] Filed: Apr. 19, 1991

[51] Int. Cl.[5] ..... A01H 5/00

[52] U.S. Cl. ..... Plt./68.1

[58] Field of Search ..... Plt./68, 68.1

*Primary Examiner*—James R. Feyrer

*Attorney, Agent, or Firm*—Foley & Lardner

[57] ABSTRACT

An aster plant named Sunshir particularly characterized by its light purple ray floret color; cup shaped flower form; single flower type; relatively light green foliage; and elongated growth habit with short side branches.

1 Drawing Sheet

The present invention comprises a new and distinct cultivar of aster hybrid; hereinafter referred to by the cultivar name Sunshir.

The new cultivar was originated from a cross made by applicant in a controlled breeding program in Mishmar Hashiva, Israel. The female, or seed, parent was a cultivar designated 34-P-12. The male, or pollen, parent was a cultivar designated 40-P-1. Both parents are hybrids of aster cultivars, species unknown.

Sunshir was discovered and selected by applicant as a flowering plant with the progeny of the stated cross in a controlled environment in Mishmar Hashiva, Israel. Asexual reproduction of the new cultivar by vegetative cuttings, as performed by applicant at Mishmar Hashiva, Israel, has demonstrated that the combination of characteristics as herein disclosed for the new cultivar are firmly fixed and retained through successive generations of asexual reproduction.

Sunshir has not been observed under all possible environmental conditions. The phenotype may vary significantly with variations in environment such as temperature, light intensity and day length, without, however, any variance in genotype. The following observations, measurements and comparisons describe plants grown in Mishmar Hashiva, Israel under conditions which closely approximate those generally used in commercial practice.

The following traits have been repeatedly observed and are determined to be basic characteristics of Sunshir which, in combination, distinguish this aster as a new and distinct cultivar:

1. The flower color is a unique light purple.
2. The flower is cup shaped even when fully open, as opposed to the normally flat shape of the inflorescence.
3. The flowers are single, with total petal count being 26.
4. The foliage color is a distinctive light green.
5. Sunshir has a generally elongated growth habit. Side branching is relatively short, with the overall appearance thereby being largely dependent on flowering off the main stem.

The new cultivar is similar to the cultivar Pink Star with regard to the inferior side branching characteristic. Otherwise, the respective cultivars are quite dissimilar. The petal color of Pink Star is a light pink, its inflorescence is flat, and its foliage a much darker green. Concerning the parent cultivars of Sunshir, the female parent has pink ray floret color and extensive side branching. The male parent also has pink ray florets, a tall growth habit, and short side branches. In view of the characteristics of the parents, the combined characteristics of Sunshir are quire surprising.

The accompanying color photographic drawings show a typical specimen plant the new cultivar.

The photograph at the top is a front perspective view of a section of a plant of Sunshir.

The bottom photo is a closeup of a flower.

The colors appearing in the photograph are as true as possible with color illustrations of this type.

In the following description, color references are made to The Royal Horticultural Society Colour Chart (RHS), except where general colors of ordinary significance are referred to. Color values were taken under artificial light conditions at approximately noon on Jan. 20, 1991 at Mishmar Hashiva, Israel.

Botanical classification: Aster hybrid cv Sunshir.

Parentage:

*Male parent.*—40-P-1.

*Female parent.*—34-P-12.

Propagation: By stem cuttings, tissue culture and division.

INFLORESCENCE

A. Capitulum:

*Form.*—Cup shaped, daisy.

*Type.*—Single.

*Diameter across face.*—2.5-3.0 cm.

B. Corolla of ray florets:

*Color (general tonality from a distance of three meters).*—Purple.

*Color (upper surface).*—69B.

*Color (under surface).*—69C.

*Number of ray florets.*—26, in single row.

C. Corolla of disc florets:

*Color (mature).*—Yellow, close to 7A.

*Color (immature).*—Yellow.

*Diameter of disc.*—0.5-0.7 cm.

D. Reproductive organs:

*Androecium.*—Yellow, 1C.

*Gynoecium.*—Greenish yellow.

E. Flowreing season: Natural flowering in Israel is approximately September 15. In photoperiodically controlled programs, flowering is after six weeks of short days following four weeks of long days.

PLANT

A. General Appearance: Elongated, due to short secondary branches in comparison to other cultivars. Length of secondary branches is half, or even less, than the length of side branches in other cultivars.

B. Height: At the commencement of flowering following short day treatment as described, plant is 80–90 cm in height.

C. Foliage:

*Color.*—146A, a unique yellow-green color.

*Shape.*—Very long and narrow; a typical leaf is 20 cm long and 1.2 cm wide.

I claim:

1. A new and distinct cultivar of aster plant named Sunshir, as illustrated and described.

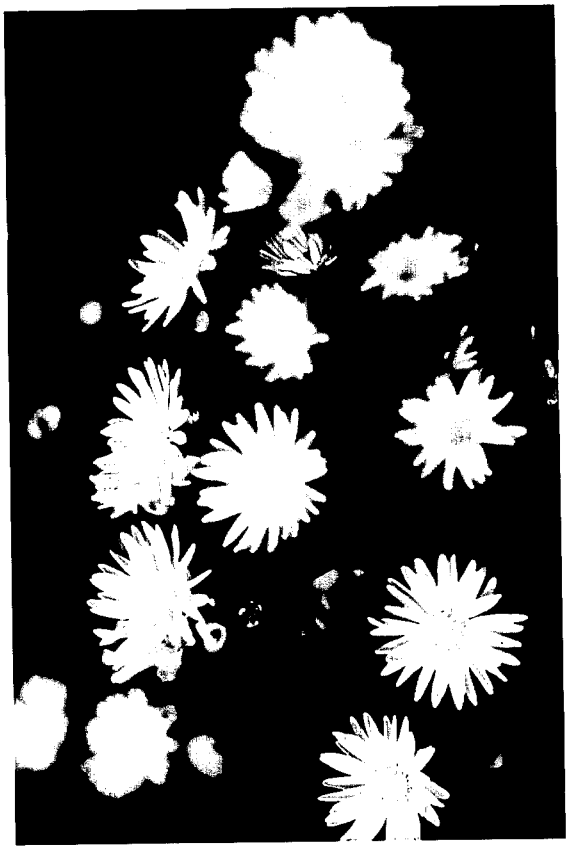
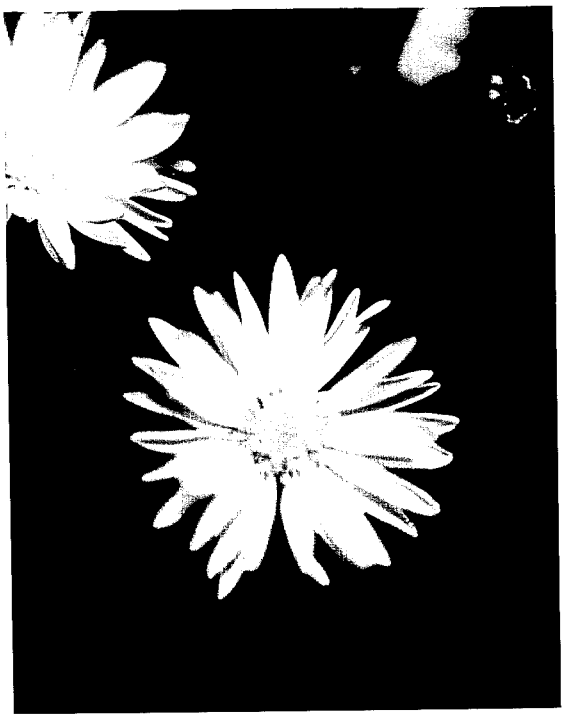

* * * * *